United States Patent [19]
Harata et al.

[11] 4,432,802
[45] Feb. 21, 1984

[54] INCLUSION COMPOUND-CONTAINING COMPOSITE

[75] Inventors: Kazuaki Harata; Satoshi Morimoto; Keishiro Tsuda, all of Ibaraki, Japan

[73] Assignee: Agency of Industrial Science & Technology Ministry of International Trade & Industry, Tokyo, Japan

[21] Appl. No.: 343,214

[22] Filed: Jan. 27, 1982

[30] Foreign Application Priority Data

Feb. 4, 1981 [JP] Japan ................. 56-15254

[51] Int. Cl.³ .................. C08L 1/02; C08L 1/08; A61K 9/36
[52] U.S. Cl. .................. 106/163 R; 106/203; 106/204; 106/205; 524/27; 524/35; 524/48; 424/35; 424/361
[58] Field of Search .............. 106/205, 203, 163, 204; 424/35, 361; 536/103; 524/35, 27, 31, 48; 252/522

[56] References Cited

U.S. PATENT DOCUMENTS 3,420,788  1/1969  Solms et al. .................. 536/103
4,138,362  2/1979  Vassiliades et al. .......... 424/35
4,339,360  7/1982  Shimizu et al. ............... 424/35

OTHER PUBLICATIONS

Chemical Abst. 68:56943f Cramer et al. 1968.
Cyclodextrins and Their Application, Akira Mifune* and Atsuyuki Shima* (Japan), pp. 116–130.

*Primary Examiner*—Theodore Morris
*Attorney, Agent, or Firm*—Oblon, Fisher, Spivak, McClelland & Maier

[57] ABSTRACT

An inclusion compound-containing composite comprises a container formed of a permeable membrane and an inclusion compound holding therein an active component and enclosed with the container. Through the membrane of the container, the composite releases the active component slowly and continuously over a long time.

6 Claims, 2 Drawing Figures

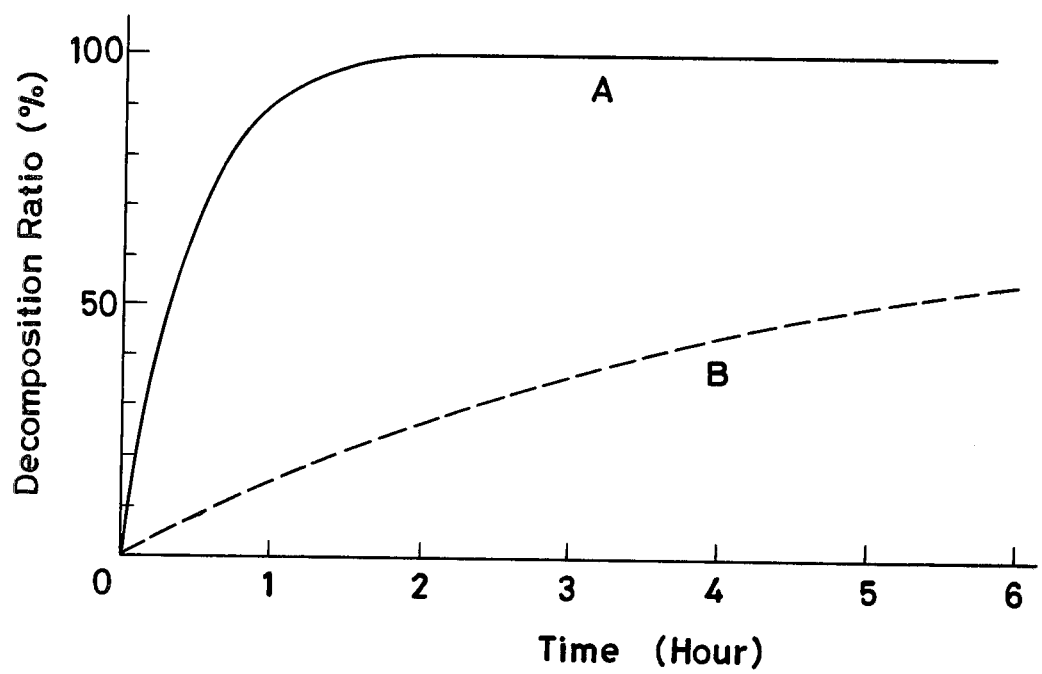
Fig_1
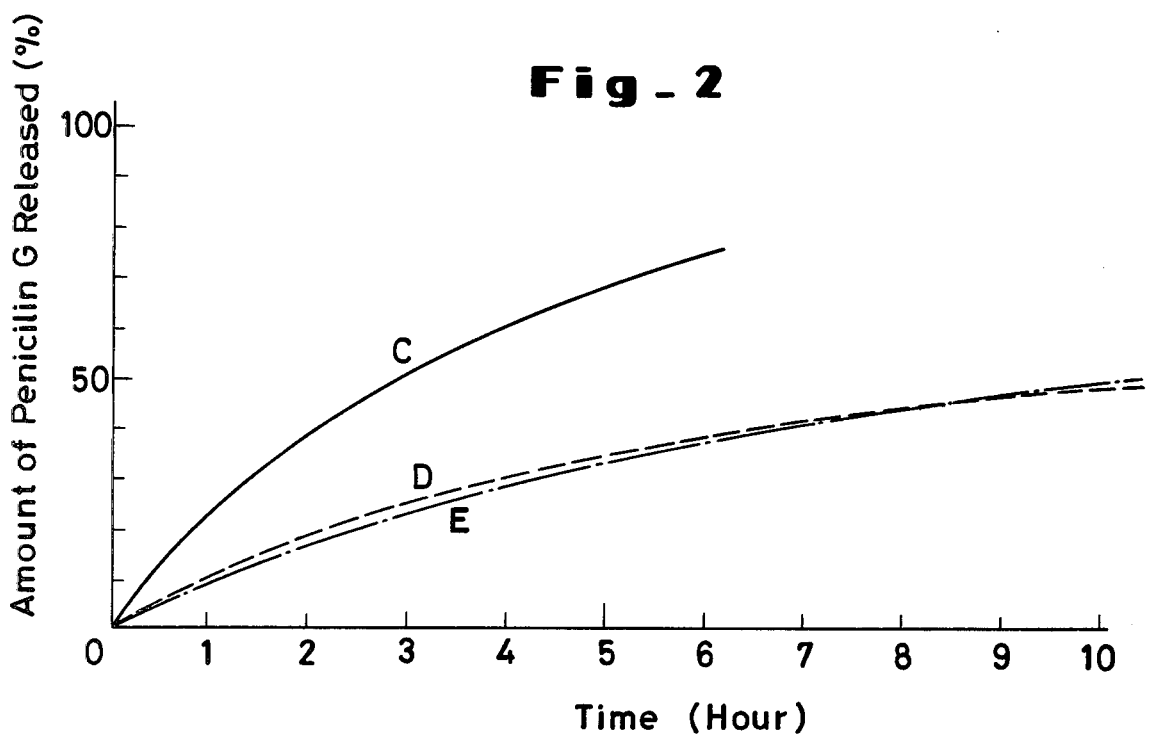
Fig_2

INCLUSION COMPOUND-CONTAINING COMPOSITE

BACKGROUND OF THE INVENTION

This invention relates to an inclusion compound holding therein an active component and allowing the active component to be released therefrom slowly and stably over a long time.

As an inclusion compound heretofore known in the art to be useful for a similar purpose, there may be cited a host-guest type inclusion compound which comprises cyclodextrin and an active component. Cyclodextrin is a cyclic oligo-saccharide having at least six D-gluclose units linked in an α-1,4 structure. This inclusion compound is soluble in water, shows good crystallinity, and possesses an ability to protect and stabilize the active component as its guest against chemical change such as oxidation and photodecomposition. Numerous studies have been made to date with a view to exploiting these advantageous properties of the inclusion compound for solubilizing sparingly soluble substances, divesting volatile substances of volatility to ensure their prolonged preservation, deodorizing offensive smelling substances, converting oily substances into finely divided solids, masking bitter tastes of foodstuffs, and materializing controlled release of aromas from perfumes and physiologically active substances from pharmaceutical compositions.

In fact, in the medicines, agricultural pesticides, perfumes, etc. available today, there are found those which are desired to release their active components steadily for prolonged periods. Inclusion compounds which hold such active components therein as their guest components hold promise of meeting this condition.

When these inclusion compounds are used as medicines, agricultural pesticides, perfumes, etc., however, they more often than not to come into substantial contact with aqueous solutions.

The formation of the inclusion compound with cyclodextrin in an aqueous solution and the dissociation of the inclusion compound into cyclodextrin and the guest component in an aqueous solution are both reactions of equilibrium. The extent to which the dissociation proceeds depends on the dissociation content, Kd, which generally ranges from 0.1 to 0.0001 and the concentrations of the components of the compound. When the inclusion compound in a solid state is dissolved in water, therefore, the dissolved inclusion compound and the guest component liberated from the compound in consequence of the dissociation are diffused and diluted so much as to expedite the dissociation. Thus, it is difficult to control the release of the guest, i.e. the active compound in the solution. This fact constitutes itself the main cause for the difficulty encountered when efforts are made to prepare an inclusion compound of cyclodextrin holding therein an active component such as a medicine, agricultural pesticide, or perfume in the hope of enabling the inclusion compound to retain the active component intact for a long time.

For the solution of this difficulty, it is imperative to curb the diffusion of the inclusion compound and the cyclodextrin component and, at the same time, enable the active component alone to be diffused and released from the inclusion compound. As one measure, the method of enclosing the inclusion compound with a container which is permeable to the guest component and impermeable to the cyclodextrin component is now under study. However, since the average molecular weight of cyclodextrin is about 1000 and that of an active substance is in the range of 100 to 500, it is not possible to obtain a selective membrane which is impervious to cyclodextrin and pervious to the active substance. Thus, the method just described has not yet been perfected.

An object of this invention is to provide an inclusion compound-containing composite which enables the active component held within the inclusion compound to be released steadily from the composite over a long period of time.

SUMMARY OF THE INVENTION

The inventors continued a diligent study to attain the object described above. They have consequently found that a cyclodextrin polymer has as high a capacity for producing an inclusion compound as cyclodextrin and that the cyclodextrin polymer and the active component can be easily separated by use of an ordinary permeable membrane. The present invention has issued from this knowledge.

To be specific, the present invention relates to an inclusion compound-containing composite which comprises a tightly closed container made partly or wholly of a permeable membrane and an inclusion compound formed of a cyclodextrin polymer incapable of permeating the membrane and an active component and enclosed within the container, whereby the active component held within the cyclodextrin polymer is released steadily from the composite over a long period of time.

BRIEF DESCRIPTION OF THE DRAWINGS

FIG. 1 is a diagram illustrating the behavior of an inclusion compound-containing composite of this invention using penicilin G as an active component in terms of time-course change of the decomposition ratio of penicilin G.

FIG. 2 is a diagram illustrating the behavior of the same composite as in FIG. 1 in terms of time-course change of the amount of release of penicilin G.

DESCRIPTION OF PREFERRED EMBODIMENTS

The active substances to which the present invention is applicable are those medicines, agricultural pesticides, perfumes, etc. which are desired to manifest their activities steadily over long periods of time and which are capable of forming inclusion compounds with the cyclodextrin polymer. Particularly the active substances suitable for the present invention are desired to be in the form of aromatic compounds such as benzene derivatives and naphthelene derivatives, compounds containing aromatic substituents, cyclic olefin compounds, and compounds possessed of alkyl groups and other similar hydrophobic groups. These active substances are believed to embrace practically all of the compounds which are capable of forming inclusion compounds with the cyclodextrin monomer.

The term "inclusion compound" as used with respect to this invention means a substance in which one compound, i.e. an active component, is trapped in the intramolecular cavities of cyclodextrin polymer.

Examples of cyclodextrin polymers which are advantageously used in this invention include high molecular compounds having at least two cyclodextrin molecules linked such as with a diether bond (—O—R—O—), a diester bond

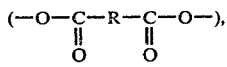

or a diamide bond

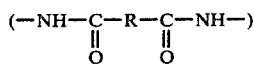

and high polymers having cyclodextrin molecules linked to existing high molecular compounds such as, for example, polystyrene and polyvinyl alcohols. There is no particular restriction on the molecular weights of these cyclodextrin polymers insofar as the molecular weight is high enough to prevent the passage of the polymer through the permeable membrane. Thus, the molecular weights are desired to be at least 10,000.

The proportion of cyclodextrin in the polymer is generally desired to be at least 10 percent by weight. Generally, the molecular weight of the guest component is about one tenth of that of cyclodextrin. The statement that the proportion of cyclodextrin in the polymer is 10 percent, therefore, implies that the proportion of the guest component is 1 percent. Actually, however, the proportion of the guest component is best determined by the use intended for the guest component, i.e. an active component.

The cyclodextrin polymer can be produced by an ordinary method known to the art using α-cyclodextrin, β-cyclodextrin, or γ-cyclodextrin as the starting material. From the commerical point of view, it is advantageous to use β-cyclodextrin, a particularly inexpensive compound, as the raw material.

The preparation of an inclusion compound from the cyclodextrin polymer and an active component is accomplished by dissolving the active component in an aqueous solution of the cyclodextrin polymer whose pH and other conditions have been adapted in advance to the active component. When the active component happens to be sparingly soluble in water, the preparation of the inclusion compound is accomplished by first dissolving this active component in an organic solvent such as methanol or acetone or in a mixed solvent consisting of such an organic solvent and water and adding the resultant solution to the aqueous solution of the cyclodextrin polymer. The organic solvent used during the preparation of the inclusion compound is expelled afterward from the finished inclusion compound by means of vacuum distillation. The concentration of the cyclodextrin polymer in the aqueous solution, though not particularly specified, is desired to fall in the range of 10 to 30 weight percent in view of the convenience of handling. The amount of the active component is not particularly limited except that it should not exceed the capacity of the cyclodextrin polymer for its inclusion. Generally, however, it is desired to fall in the range of 0.05 to 0.20 weight part per weight part of the cyclodextrin polymer. The reason for the desirability of this range is that the amount of the cyclodextrin polymer which does not participate in the inclusion of the active component is excessively large when the amount of the active component is less than 0.05, while the amount of the active component which escapes inclusion by the cyclodextrin polymer is excessively large when the amount of active component is greater than 0.20.

The aqueous solution of the inclusion compound of the cyclodextrin polymer and the active component prepared as described above can be directly sealed in a container formed of permeable membrane. Otherwise, the aqueous solution may be converted into a solid or finely divided particles by means of vacuum evaporation and sealed in the same container. Thus is obtained an inclusion compound-containing composite which releases the active component steadily over a long period of time.

As the permeable membrane mentioned above, any of the known permeable membranes can be effectively used insofar as it possesses strength enough to withstand possible increase in the pressure of osmosis within the container. Examples of membranes which can advantageously be used in this invention include membranes formed of cellulose and derivatives thereof, polyvinyl alcohols, and polyamides. A membrane of cellulose or acetyl cellulose can be used particularly advantageously.

When the container is only partially formed of a permeable membrane, the portion of the container which is not a permeable membrane may be formed of a plastic material, glass, or metal on condition that the material thus used should not produce adverse effects upon the inclusion compound enclosed within and should be capable of being intimately joined with the permeable membrane. The proportion of the permeable membrane to the entire container is variable with the use intended for the finished inclusion compound-containing composite. Practically, this proportion is at least 5 percent of the entire surface of the container.

The enclosure of the inclusion compound in the container can be accomplished by any of the ordinary methods heretofore known to the art. For example, the method which comprises preparatorily producing a container formed wholly or partially of permeable membrane and subsequently sealing the inclusion compound in this container or the method of microcapsulation which comprises converting the liquid or solid inclusion compound into finely divided particles and subsequently coating these particles with permeable membrane by some physical or chemical process is usable for this purpose.

The inclusion compound-containing composite of the present invention is such that the active component which, in conjunction with the cyclodextrin polymer, forms the inclusion compound is enclosed within the tightly closed container of permeable membrane. Therefore the active component is protected over long periods against chemical change such as oxidation and decomposition. The dissociation of the inclusion compound into the cyclodextrin polymer and the active component proceeds only very slowly because the cyclodextrin polymer is not diffused out of the container. Even if the inclusion compound should come into contact with an aqueous solution, the release of the active component proceeds very slowly. Thus, the composite releases the active component steadily on a fixed level over a long period of time.

Now, the present invention will be described more specifically below with reference to referential experiments and a working example.

Referential Experiment 1: (Synthesis of cyclodextrin polymer)

Ten g of powdered α-cyclodextrin and 5 g of water were blended. The resultant mixture was stirred with 4 ml of a 30-percent aqueous sodium hydroxide solution and 50 mg of sodium borohydride until homogeneous solution. While the resultant solution was heated at 60° C. and vigorously stirred, 4 ml of epichlorohydrin was added dropwise thereto over a period of 30 minutes. The stirring was continued for two hours after the end of the addition. The resultant solution was held at 60° C. for one hour, then cooled, added with 10 ml of water, sealed in a cellulose dialysis tube, and left standing overnight under water to remove, by dialysis, sodium hydroxide, sodium chloride, and the portion of the cyclodextrin polymer having a molecular weight of less than 10,000. After the end of the dialysis, the solution was freed of water by vacuum distillation to afford 8.5 g of α-cyclodextrin polymer having a molecular weight of more than 10,000.

When the procedure described above was repeated using 9 g of β-cyclodextrin, 5 ml of a 40-percent aqueous sodium hydroxide solution, 50 mg of sodium borohydride, and 3 ml of epichlorohydrin, there was obtained 8.2 g of β-cyclodextrin polymer having a molecular weight of more than 10,000. Referential Experiment 2:

Two g of the β-cyclodextrin polymer obtained in Referential Experiment 1 was dissolved in 100 ml of an aqueous hydrochloric acid solution and adjusted to pH 2.0. Separately, 40 mg of penicillin G was dissolved in 50 ml of water. Then, the two solutions were mixed by means of a stopped flow attachment installed in a spectro-polarimeter to produce an inclusion compound consisting of β-cyclodextrin polymer and penicilin G. The compound was tested for time-course change of circular dichroism at 230 mm to determine the speed of decomposition of penicilin G.

As a control, an aqueous solution of pH 2 not containing β-cyclodextrin polymer and an aqueous solution of penicilin G were mixed in the same manner as described above. The resultant solution was tested for the speed of decomposition of penicilin G.

The results are shown in FIG. 1. In the graph of FIG. 1, the vertical axis is the scale of the decomposition ratio (%) of penicilin G and the horizontal axis is the scale of the time elapse (in hours). The curve A represents the data obtained of the solution not containing the β-cyclodextrin polymer, and it shows that penicilin G was thoroughly decomposed in the pH 2 aqueous solution in a matter of about two hours. The curve B represents the data obtained of the solution containing the inclusion compound employing the β-cyclodextrin polymer, and it shows that decomposition of 50 percent of penicilin G took about five hours.

EXAMPLE 1

The α- and β-cyclodextrin polymers obtained in Referential Experiment 1 were each prepared in the form of a 10-percent aqueous solution. To 10 cc of the aqueous solution, 40 mg of penicilin G was added to produce an inclusion compound. A 1-ml portion of the aqueous solution containing the produced inclusion compound was sealed in a cellulose dialysis tube impervious to molecules having molecular weights of more than 3,500. The cellulose dialysis tube was immersed in 200 ml of water. The external solution was stirred and circulated by a pump through a flow cell installed within a spectrophotometer, to determine the concentration of the penicilin G released into the external solution by measuring the absorbancy at 230 nm.

As a control, an aqueous solution containing penicilin G in the same concentration as described above was sealed in a dialysis tube. By following the procedure described above, the external solution was tested to determine the concentration of the penicilin G released into the external solution.

The results are shown in FIG. 2. In the graph of FIG. 2, the vertical axis is the scale of the amount of penicilin G released (%) and the horizontal axis is the scale of the time elapse (in hours). The curve C represents the data obtained of the solution not containing the cyclodextrin polymer, and it shows that 50 percent of the whole amount of penicilin G was released over a period of three hours. The curve D represents the data obtained of the solution containing the α-cyclodextrin polymer and the curve E represents the data obtained of the solution containing the β-cyclodextrin polymer. In either of these cases, penicilin G was released gradually at a fixed level and the release of 50 percent of the whole amount of penicilin G took ten hours.

What is claimed is:

1. An inclusion compound-containing composite, comprising a closed container formed partially or wholly of permeable membrane and an inclusion compound enclosed by said container, wherein said enclosed inclusion compound consists of a water-soluble cyclodextrin polymer incapable of permeating said membrane and an active component capable of permeating said membrane, whereby the composite releases said active component steadily over a long period of time.

2. The inclusion compound-containing composite according to claim 1, wherein the cyclodextrin polymer is produced by causing a multiplicity of cyclodextrin molecules to be linked mutually to form a polymer or by causing cyclodextrin molecules to be linked to a high molecular weight compound.

3. The inclusion compound-containing composite according to claim 1, wherein the permeable membrane is preponderantly selected from the group consisting of cellulose, derivatives of cellulose, polyvinyl alcohols, and polyamides.

4. The inclusion compound-containing composite according to claim 1, wherein the inclusion compound is enclosed in the form of an aqueous solution in the container.

5. The inclusion compound-containing composite according to claim 1, wherein the inclusion compound is enclosed in the form of a solid or powder in the container.

6. The inclusion compound-containing composite according to claim 1, wherein the cyclodextrin polymer has a molecular weight of at least 10,000.

* * * * *